United States Patent
Williams et al.

(10) Patent No.: US 11,304,744 B2
(45) Date of Patent: Apr. 19, 2022

(54) BIPOLAR ELECTROSURIGAL INSTRUMENTS

(71) Applicant: GYRUS MEDICAL LIMITED, Cardiff (GB)

(72) Inventors: Wayne Williams, Penarth (GB); Lewis Jones, Cardiff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 312 days.

(21) Appl. No.: 16/413,756

(22) Filed: May 16, 2019

(65) Prior Publication Data

US 2019/0380770 A1    Dec. 19, 2019

(30) Foreign Application Priority Data

Jun. 13, 2018  (GB) ..................................... 1809684

(51) Int. Cl.
  *A61B 18/12* (2006.01)
  *A61B 18/14* (2006.01)
  *A61B 18/00* (2006.01)

(52) U.S. Cl.
  CPC ...... *A61B 18/1445* (2013.01); *A61B 18/1206* (2013.01); *A61B 2018/0063* (2013.01); *A61B 2018/00589* (2013.01); *A61B 2018/00755* (2013.01); *A61B 2018/00875* (2013.01); *A61B 2018/126* (2013.01)

(58) Field of Classification Search
  CPC ............ A61B 18/1206; A61B 18/1233; A61B 18/1445; A61B 2018/00666; A61B 2018/00755; A61B 2018/00875; A61B 2018/126
  See application file for complete search history.

(56) References Cited

U.S. PATENT DOCUMENTS

| | | | |
|---|---|---|---|
| 5,540,684 A | | 7/1996 | Hassler, Jr. |
| 5,558,671 A | * | 9/1996 | Yates ............... A61B 17/07207 606/38 |
| 2002/0133152 A1 | * | 9/2002 | Strul .................. A61B 18/1445 606/50 |
| 2003/0158551 A1 | | 8/2003 | Paton et al. |
| 2007/0173804 A1 | | 7/2007 | Wham et al. |
| 2011/0238062 A1 | | 9/2011 | Koss et al. |
| 2013/0296840 A1 | * | 11/2013 | Condie .............. A61B 18/1492 606/33 |
| 2014/0025061 A1 | | 1/2014 | Benamou |

(Continued)

OTHER PUBLICATIONS

Nov. 26, 2018 Search Report issued in European Patent Application No. GB1809684.2.

*Primary Examiner* — Daniel W Fowler
(74) *Attorney, Agent, or Firm* — Oliff PLC

(57) ABSTRACT

A bipolar surgical instrument comprises a body, first and second opposed jaws located at the distal end of a shaft, the first jaw being movable with respect to the second jaw between an open position in which the first and second jaws are spaced apart from one another, and a closed position in which the first and second jaws are adjacent one another. The first and second elongate jaw members have respective first and second electrodes. A controller is operable to determine a boiling point for tissue between the jaws using a measure of impedance therebetween.

12 Claims, 6 Drawing Sheets

(56) References Cited

U.S. PATENT DOCUMENTS

2015/0289925 A1* 10/2015 Voegele ............. A61B 18/1233
                                                                606/38
2016/0367308 A1* 12/2016 Takami ................. A61B 18/12
2017/0196621 A1*  7/2017 Wilson ............... A61B 18/1445

* cited by examiner

BIPOLAR ELECTROSURIGAL INSTRUMENTS

The present invention relates to bipolar electrosurgical instruments.

BACKGROUND OF THE INVENTION

Bipolar surgical instruments are used to clamp and seal tissue, such as blood vessels, during surgical procedures. Clamping is typically achieved using a pair of opposed jaws that are remotely operable to clamp around the vessel being sealed. Sealing is typically achieved using application of radio frequency energy delivered to the tissue being sealed by electrodes mounted on the opposed jaws of the instrument.

Existing designs of such instruments may not provide optimal transfer of electrical power to the tissue, and so may not provide optimal tissue sealing. For example, it is desirable to have acceptably short sealing times.

It is, therefore, desirable to provide an improved bipolar surgical instrument that, at least partially, addresses these drawbacks.

SUMMARY OF THE INVENTION

Aspects of the present invention are set out in the attached claims.

According to one exemplary aspect, there is provided an electrosurgical system comprising a bipolar electrosurgical instrument comprising a body; an elongate shaft attached to the body, the elongate shaft extending to a distal end; first and second elongate jaw members located at the distal end of the elongate shaft, and carrying respective first and second electrodes, the jaw members being movable relative to one another between an open position in which the first and second electrodes are spaced apart from one another, and a closed position in which the first electrode is adjacent the second electrode; and a power cable having a pair of electrically conductive elements, and having a first end for connection with a source of radio frequency electromagnetic energy, and a second end for connection to the first and second electrodes; and a waveform generator connected with the power cable of the bipolar electrosurgical instrument and comprising a radio frequency signal generator operable to supply a radio frequency signal to the first and second electrodes via the power cable; and a controller operable to control operation of the radio frequency signal generator, in dependence upon a received control input, wherein the controller is operable, in a heating stage to control the radio frequency generator to supply a radio frequency signal at a controlled voltage level to the first and second electrodes, the controlled voltage level starting at a starting voltage at a heating start time, and ending at a final voltage at a heating end time; to measure an impedance between the first and second electrodes during supply of the controlled voltage level; to detect a minimum measured impedance between the first and second electrodes during the heating stage, and to store that minimum measured impedance as a minimum recorded impedance measurement for the heating stage; and to determine the heating end time as that time when the recorded impedance measurement for the heating stage is greater than the minimum impedance by a threshold amount, wherein the controller is operable, in a sealing stage following the heating stage: to supply a radio frequency signal at a predetermined sealing voltage level to the first and second electrodes for a predetermined sealing time period having a sealing end time; to measure an impedance level between the first and second electrodes at the sealing end time; to compare the measured impedance with a predetermined reference impedance to produce a comparison signal; and to determine a next mode of operation for the radio frequency signal generator in dependence upon such a comparison signal, and wherein the controller is operable, subsequent to the sealing stage: to repeat the heating and sealing stages whilst the minimum recorded impedance measurement for such a repeated heating stage is lower than or equal to the overall minimum impedance measurement of previous heating stages, and to end the heating and sealing stages when the minimum recorded impedance measurement for a repeated heating stage is greater than the overall minimum impedance measurement of previous heating stages.

In one example, the controller is operable, in an initialisation stage prior to the heating stage to control the radio frequency signal generator to supply a radio frequency signal of a predetermined initial power level to the first and second electrodes for a predetermined initial time period having an end time; to measure a voltage level between the first and second electrodes at the end time; and to store such a measured voltage as the starting voltage for the heating stage.

In one example, the controller is operable, wherein the controller is operable, in a completion stage subsequent to the ending of the heating and sealing stages to control the radio frequency signal generator to apply a radio frequency signal at a predetermined completion voltage level, lower than the predetermined sealing voltage level, for a predetermined completion time period; and to end supply of such radio frequency signals.

In one example, the controller is operable to measure electrical current supplied to the first and second electrodes to generate a measured current signal, and to detect a short circuit between the first and second electrodes if the measured current signal indicates electrical current supplied to the first and second electrodes exceeds a first predetermined value for at least a predetermined time period.

In one example, the threshold value is an absolute value of impedance, and in another example, the threshold value is a relative value related to the minimum impedance measurement.

According to another exemplary example, there is provided a method of operating an electrosurgical system comprising a bipolar electrosurgical instrument comprising a body; an elongate shaft attached to the body, the elongate shaft extending to a distal end; first and second elongate jaw members located at the distal end of the elongate shaft, and carrying respective first and second electrodes, the jaw members being movable relative to one another between an open position in which the first and second electrodes are spaced apart from one another, and a closed position in which the first electrode is adjacent the second electrode; and a power cable having a pair of electrically conductive elements, and having a first end for connection with a source of radio frequency electromagnetic energy, and a second end for connection to the first and second electrodes; and a waveform generator connected with the power cable of the bipolar electrosurgical instrument and comprising a radio frequency signal generator operable to supply a radio frequency signal to the first and second electrodes via the power cable; and a controller operable to control operation of the radio frequency signal generator, in dependence upon a received control input, wherein the method comprises a heating stage comprising controlling the radio frequency generator to supply a radio frequency signal at a controlled voltage level to the first and second electrodes, the controlled voltage level starting at the starting voltage at an heating start time, and ending at a final voltage at an heating end time; measuring an impedance between the first and second electrodes during supply of the controlled voltage level; detecting a minimum measured impedance between the first and second electrodes during the heating stage, and to store that minimum measured impedance as a minimum recorded impedance measurement for the heating stage; and determining the heating end time as that time when the recorded impedance measurement for the heating stage is greater than the minimum impedance by a threshold amount, wherein the method further comprises, subsequent to the heating stage, a sealing stage comprising: supplying a radio frequency signal at a predetermined sealing voltage level to the first and second electrodes for a predetermined sealing time period having a sealing end time; measuring an impedance level between the first and second electrodes at the sealing end time; comparing the measured impedance with a predetermined reference impedance to produce a comparison signal; and determining a next mode of operation for the radio frequency generator in dependence upon such a comparison signal; and wherein the method further comprises, subsequent to the sealing stage, repeating the heating and sealing stages whilst the minimum recorded impedance measurement for such a repeated heating stage is lower than or equal to the overall minimum impedance measurement of previous heating stages, and ending the heating and sealing stages when the minimum recorded impedance measurement for a repeated heating stage is greater than the overall minimum impedance measurement of previous heating stages.

In one example, such a method further comprises, in advance of the heating stage, an initialisation stage comprising supplying a radio frequency signal of a predetermined initial power level to the first and second electrodes for a predetermined initial time period having an initialisation end time; measuring a voltage level between the first and second electrodes at the initialisation end time; and storing such a measured voltage as the starting voltage for the heating stage.

In one example, such a method further comprises, subsequent to the sealing stage, a completion stage comprising controlling the radio frequency signal generator to apply a radio frequency signal at a predetermined completion voltage level, lower than the predetermined sealing voltage level, for a predetermined completion time period; and ending supply of such radio frequency signals.

In one example, such a method further comprises measuring electrical current supplied to the first and second electrodes to generate a measured current signal, and detecting a short circuit between the first and second electrodes if the measured current signal indicates electrical current supplied to the first and second electrodes exceeds a first predetermined value for at least a predetermined time period.

In one example, the threshold value is an absolute value of impedance, and in another example, the threshold value is a relative value related to the minimum impedance measurement.

DETAILED DESCRIPTION OF THE PREFERRED EMBODIMENTS

Figure 1:
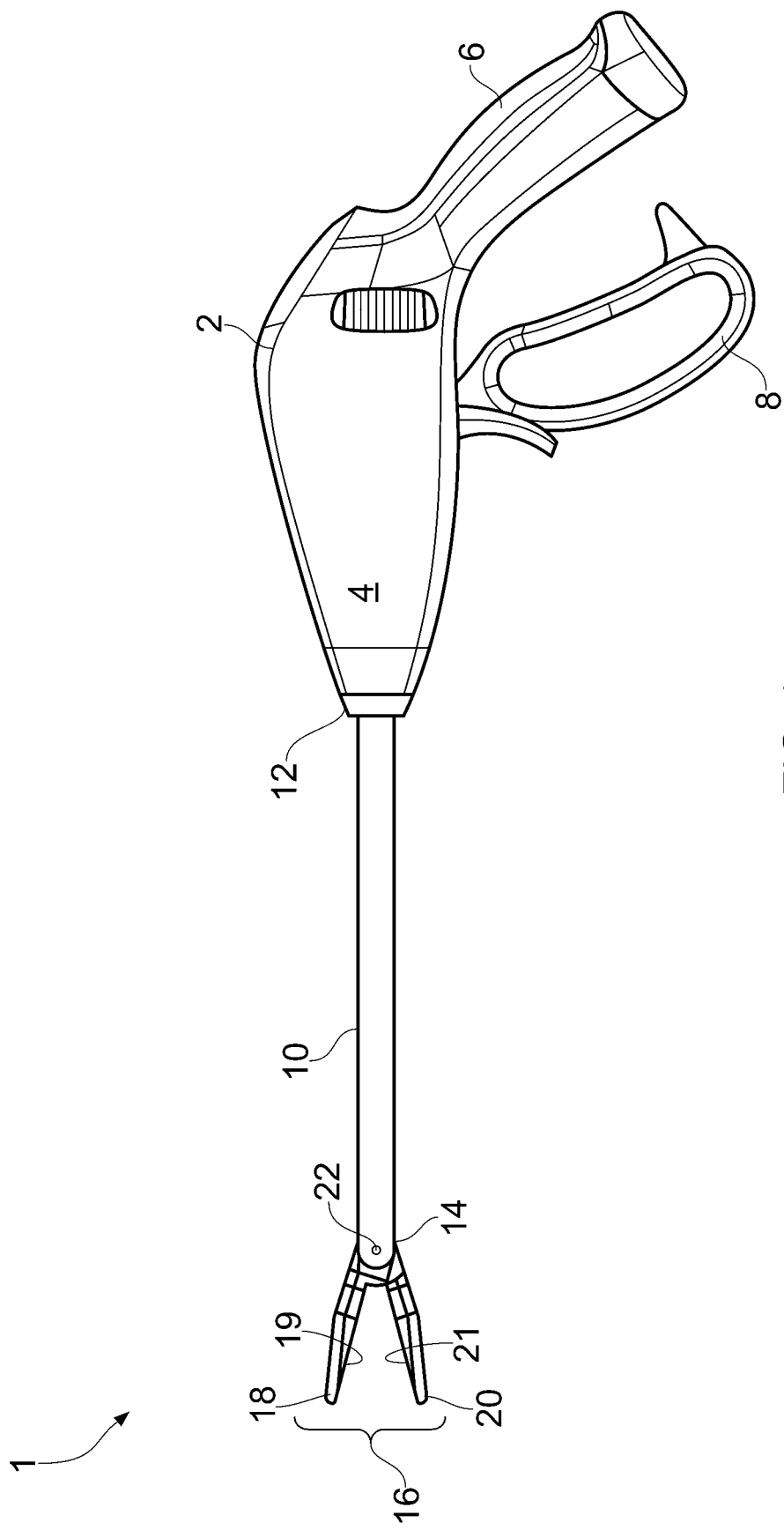
FIGS. 1 and 2 show side views of a bipolar surgical instrument embodying one aspect of the present invention in open and closed positions respectively.
Figure 2:
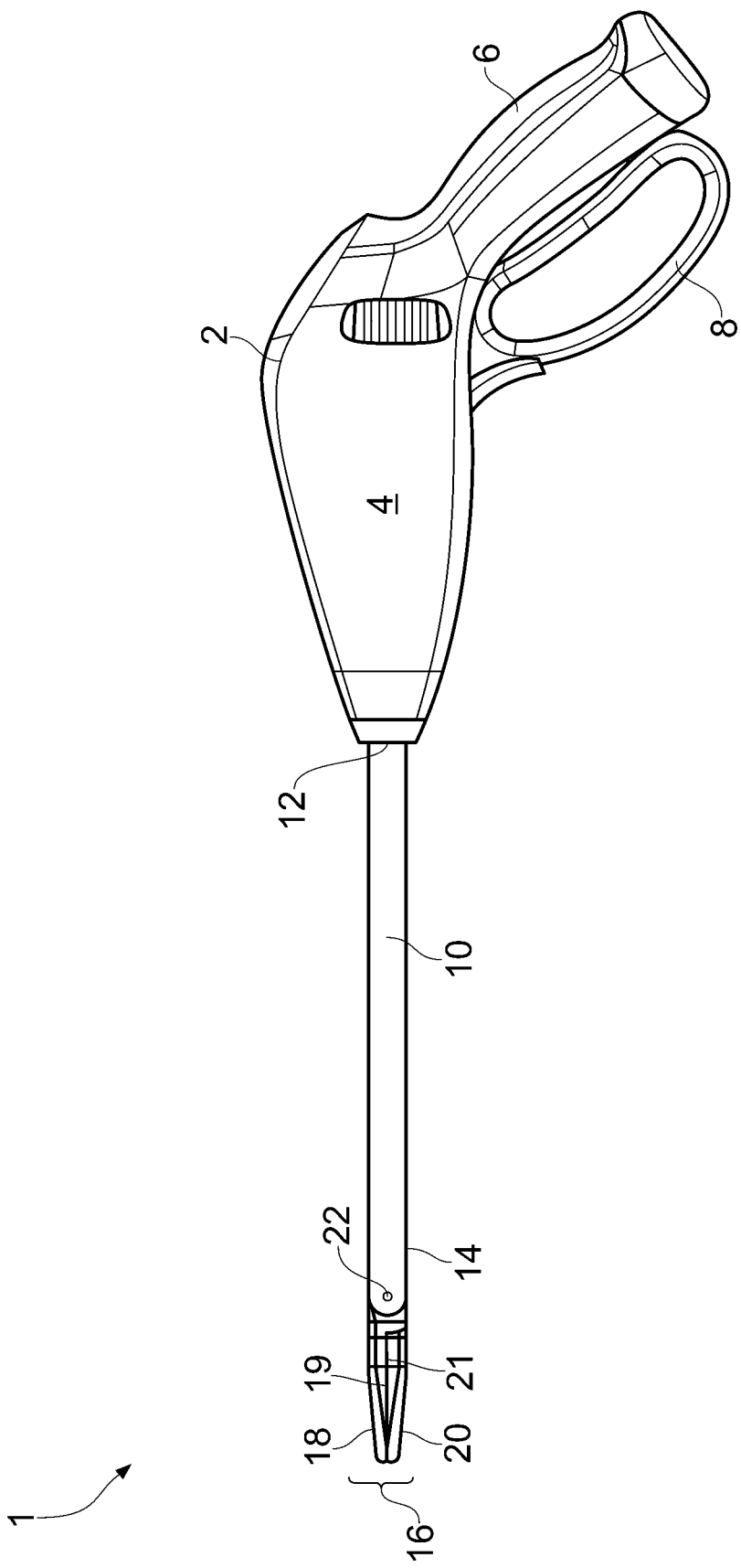

An example bipolar surgical instrument 1 is shown schematically in FIGS. 1 and 2. FIG. 1 illustrates an open position of the instrument 1, and FIG. 2 illustrates a closed position thereof.

The instrument 1 comprises a body 2 having a main housing 4 from which a fixed grip 6 extends. The fixed grip 6 is held during use by the operator of the instrument 1. A movable actuation grip 8 is movably mounted on the main housing 4 of the body 2. An elongate shaft 10 is attached to the main housing 4 of the body 2 and extends from a proximal end 12 at the main housing 4, to a distal end 14 of the shaft 10. The shaft 10 defines a longitudinal axis therealong, and an elongate passage extends from the proximal end 12 to the distal end 14 of the shaft 10.

A pair 16 of opposed jaws are located at the distal end 14 of the shaft 10. The pair 16 of jaws comprises a first jaw 18 and a second jaw 20. In the example of FIGS. 1 and 2, the first and second jaws 18 and 20 are pivotally mounted on a jaw pivot 22. The first and second jaws 18 and 20 are pivotable about the jaw pivot 22, between an open position (as shown in FIG. 1) in which the jaws 18 and 20 are separated from one another, and a closed position (as shown in FIG. 2) in which the jaws 18 and 20 are adjacent one another. In another example of a bipolar instrument embodying the present invention, only one of the jaws is movable. In another example, the movable jaw or jaws may be movable in any suitable manner, for example linearly, or in a combination of rotation and linear movement. The exact nature of the movement of the jaws is not important in the context of the present invention.

The first and second jaws 18 and 20 carry first and second electrodes 19 and 21 respectively. The first and second electrodes 19 and 21 are arranged to apply radio frequency electromagnetic energy to vessel held between the first and second jaws 18 and 20.

In use, the operator of the instrument 1 moves the actuation grip 8 from a first position (shown in FIG. 1) to a second position (shown in FIG. 2) in order to move the jaws 18 and 20 from the open position to the closed position. During an operation, vessel to be sealed is held between the jaws 18 and 20 in the closed position for a predetermined time period, with pressure applied by the operator, and with radio frequency energy applied to the vessel. The radio frequency energy serves to seal the held vessel.

Figure 3:
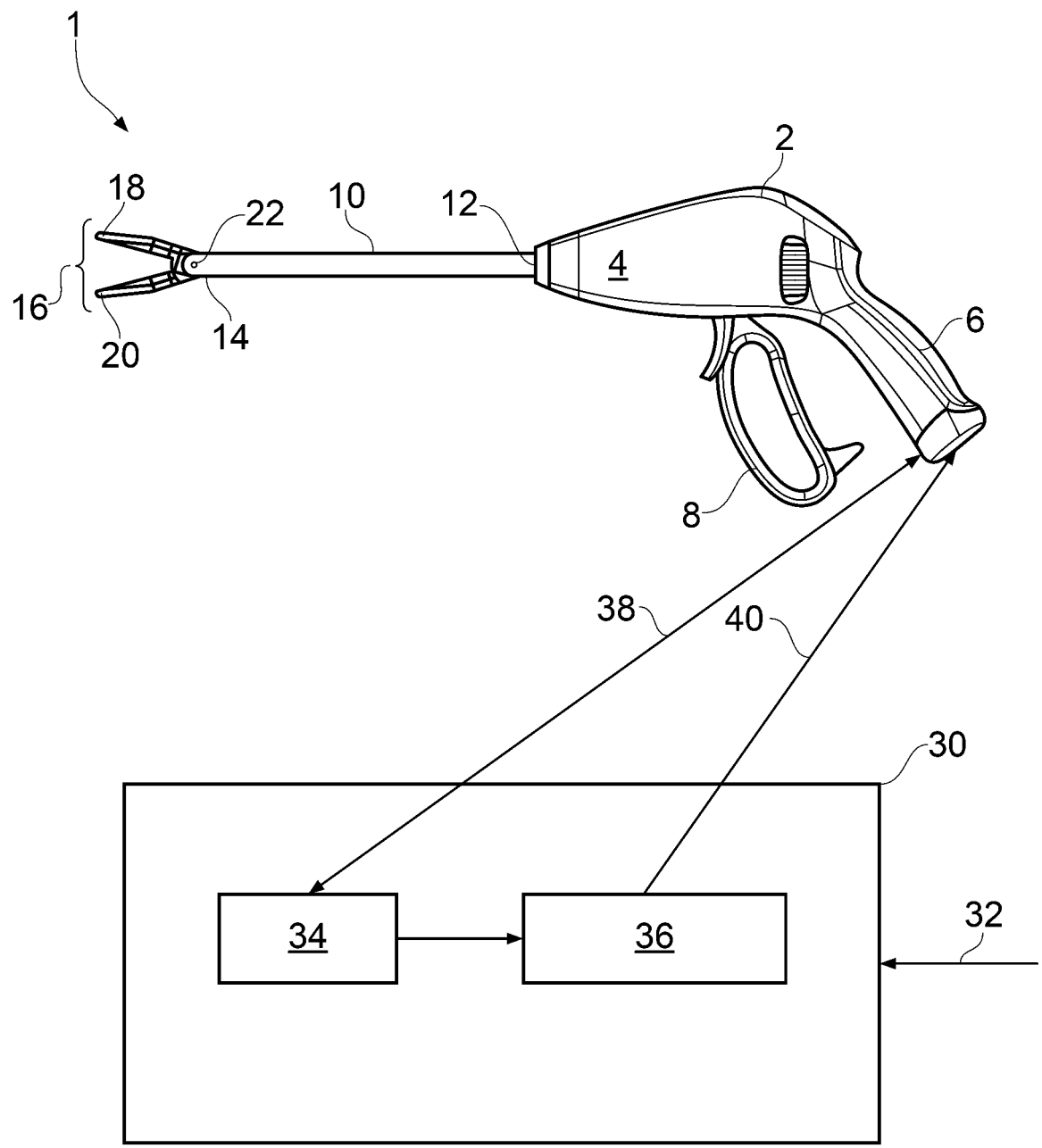
FIG. 3 illustrates a controller for use with a bipolar surgical instrument.

FIG. 3 illustrates the instrument 1 connected with a waveform generator 30. The waveform generator 30 receives an electrical power supply 32 and includes a controller 34 and a radio frequency signal generator 36. A control cable 38 connects the controller 34 to control inputs located, in one example, in or on the instrument 1. The control inputs may be located separately from the instrument 1, for example as a foot switch. A measurement cable may also be provided to provide a path for measurement signals.

The controller 34 is operable to control the signal generator 36 which is connected by power cable 40 to the instrument 1. The power cable 40 includes a pair of conductors that are connected to respective ones of the first and second electrodes 19 and 21 of the instrument 1. Upon reception of an appropriate control signal, for example from an operating switch such as a foot pedal, the controller 34 causes the signal generator 36 to supply a radio frequency electrical output signal via the power cable 40 to the first and second electrodes 19 and 21. One of the electrodes is defined as the active electrode and one as the return electrode.

The output radio frequency electrical signal in a system embodying the principles of present invention applies a desired sealing waveform to the vessel being held between the first and second jaws 18 and 20, which will be described below.

Figure 4:
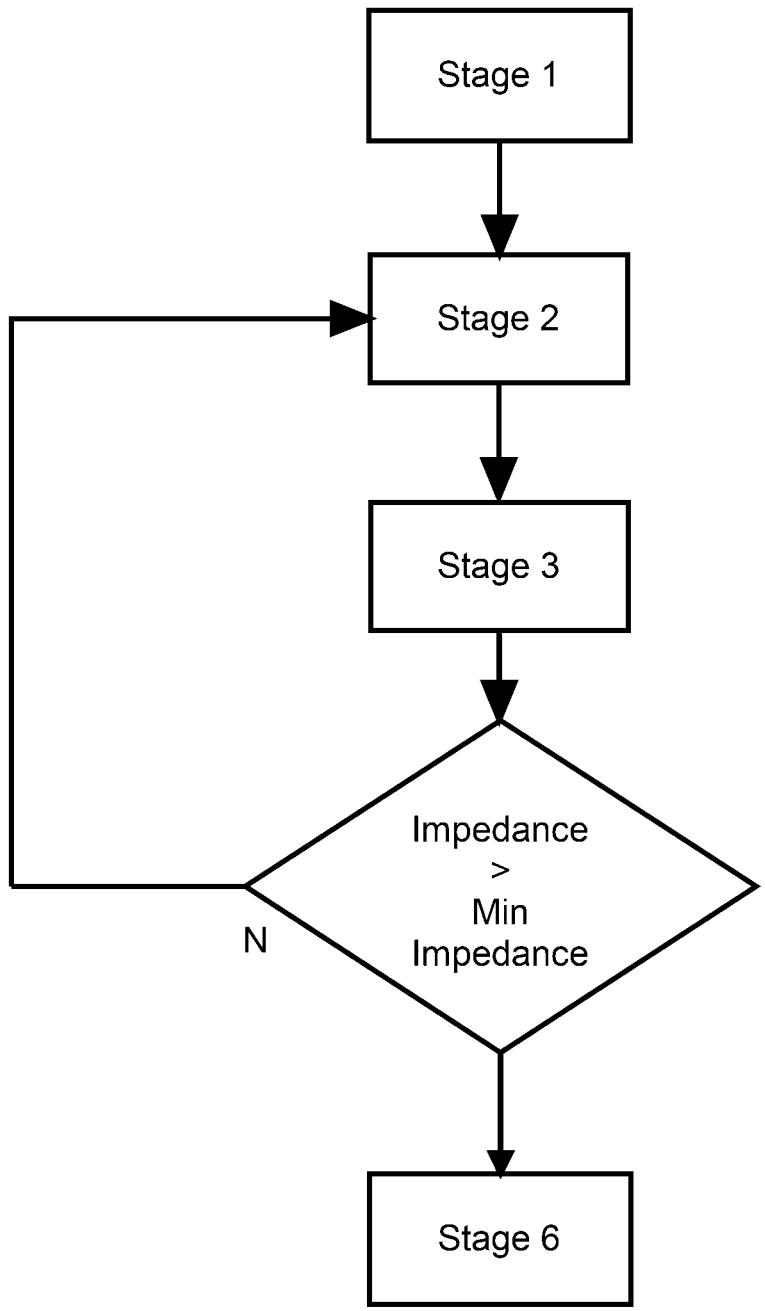
FIG. 4 is a flowchart illustrating steps in a method embodying another aspect of the present invention.
Figure 5:
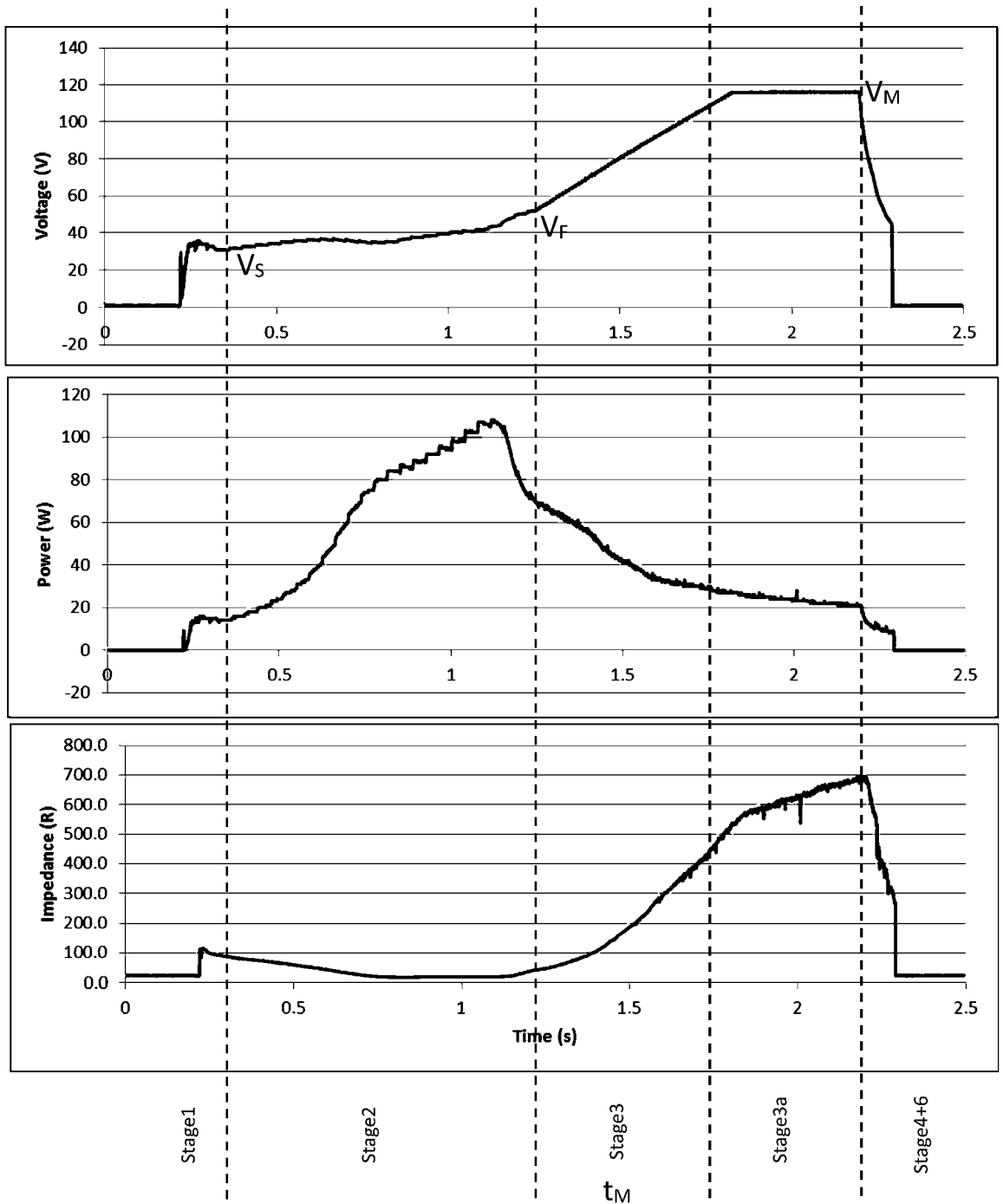
FIGS. 5 and 6 show graphs illustrating voltage, current, power and impedance against time for a bipolar surgical instrument operated in accordance with the method of FIG. 4.
Figure 6:
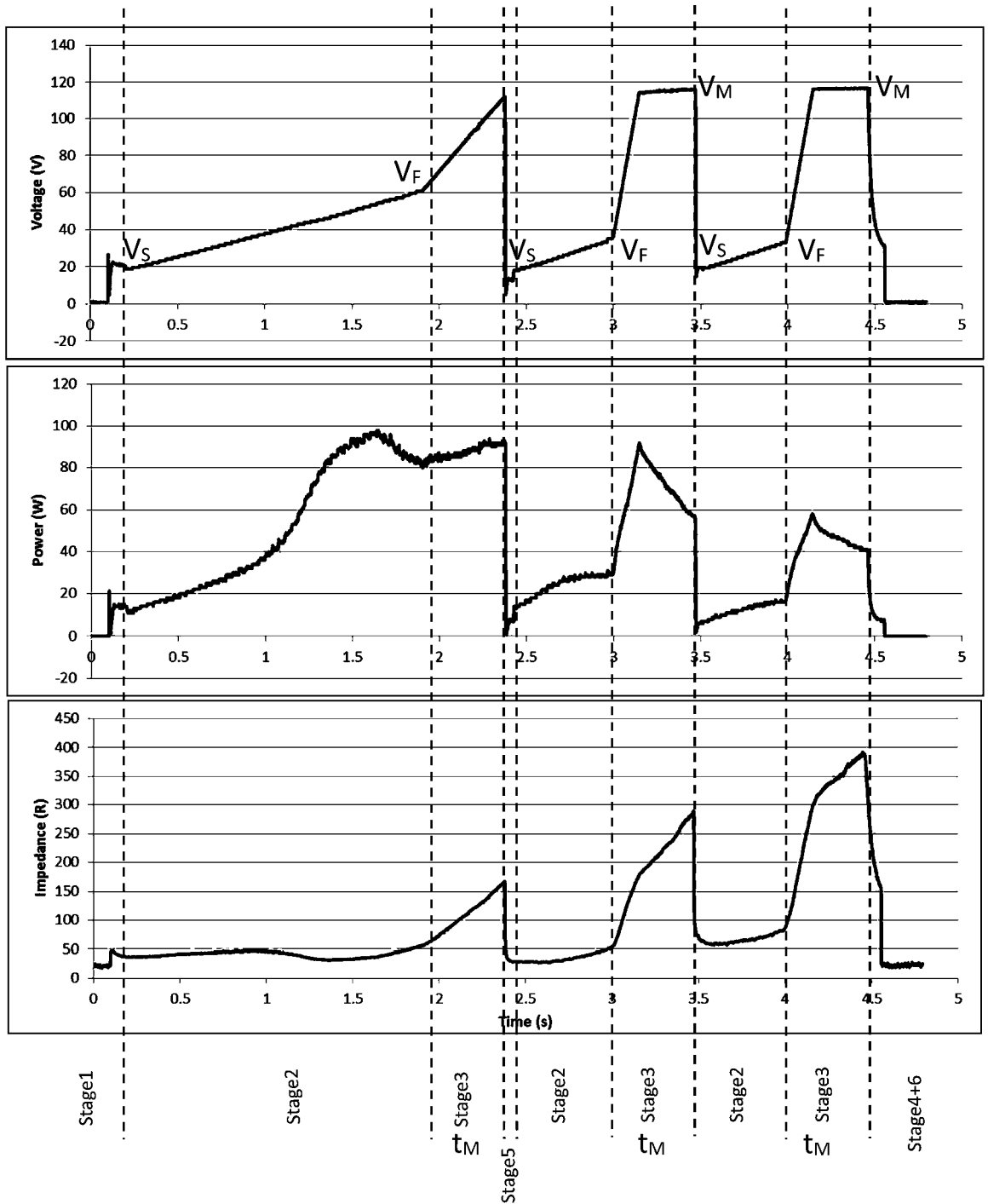

A method embodying one aspect of the present invention will now be described with reference to the flowchart of FIG. 4, and the graphs of FIGS. 5 and 6. The graphs of FIGS. 5 and 6 show exemplary voltage and power of the applied radio frequency signal, and exemplary measured impedance across the first and second electrodes of the surgical instrument 1.

In an embodiment of the present invention, stage 1 of the application of the radio frequency energy is an initial low-power stage, in which an appropriate starting voltage is determined. In stage 1, a constant power is applied to the vessel for a period of time short enough not to alter substantially the characteristics of the vessel. The constant power level may be in the range of up to 20 W, and may be applied for up to 200 ms. After the time period of application of the constant power level, the voltage required to maintain the initial power level is measured and is then used as the starting voltage $V_S$ for the vessel heating and sealing process.

Stage 2 applies a slow-ramping voltage across the first and second electrodes, which ramps up from the starting voltage determined in stage 1. Preferably, the applied voltage ramps in a linear manner. In one example, the voltage is ramped up from the starting voltage $V_S$ in discrete steps every millisecond. In one example, the voltage ramp rate is 0.02V/ms.

In order to determine when the boiling point of the vessel has been reached, without the need for a direct temperature measurement, the impedance of the vessel held between the jaws is measured. As pressure is applied to the vessel between the jaws, and the applied voltage increases, initially the impedance of the vessel drops. After an undefined time period, the vessel starts to coagulate, and the impedance increases from a minimum value.

In an initial stage 2 of the present process, impedance is measured effectively continually, for example every 1 ms, as the applied voltage is ramped up. Each new impedance measurement is compared with a stored minimum impedance measurement for the present stage 2, and, if the new impedance measurement is lower than that previous impedance measurement, the new impedance measurement is stored as the minimum impedance measurement for the initial stage 2. The impedance measurements continue during the initial stage 2 until the initial stage 2 is complete. The stored minimum impedance measurement at the end of the initial stage 2 is then considered to be the minimum impedance level for the initial stage 2 of the process.

The initial stage 2 is considered to be completed when the new impedance measurement is greater than the stored minimum impedance measurement by a predetermined value. For example, the predetermined value may be an absolute value of impedance, for example 20 R, or may be a proportion of the minimum impedance value, such as 10%. When the initial stage 2 of the process is completed, then stage 3 commences.

Stage 3 of the process is a sealing and size detection process and takes place over a fixed hold time period $t_M$, for example 500 ms. During stage 3, the applied voltage is ramped-up from the final voltage $V_F$ applied at the end of stage 2, at a rate faster than that used during stage 2, towards a maximum voltage $V_M$, for example 115V. The applied voltage at the end of the stage 3 may not have reached the maximum voltage $V_M$, for example if $V_F$ is lower than expected, and the rate of increase of the applied voltage is not high enough to reach $V_M$. At the end of the hold time period, the impedance of the vessel is measured.

When the present stage 3 is completed, then a further stage 2 of the process is repeated. During the repeated stage 2, impedance is again measured effectively continually, for example every 1 ms, as the applied voltage is ramped up. As for the initial stage 2, each new impedance measurement is compared with the minimum impedance measurement for the repeated stage 2, and if the new impedance measurement is lower than that previous impedance measurement, the new impedance measurement is stored as the minimum impedance measurement for the repeated stage 2.

The impedance measurements continue during the repeated stage 2 until the repeated stage 2 is complete. The stored minimum impedance measurement at the end of the repeated stage 2 is then considered to be the minimum impedance level for the repeated stage 2 of the process.

The repeated stage 2 is considered to be completed when the new impedance measurement is greater than the stored minimum impedance measurement for the repeated stage 2 by a predetermined value. For example, the predetermined value may be an absolute value of impedance, for example 20 R, or may be a proportion of the minimum impedance value, such as 10%.

The minimum impedance measurement for the repeated stage 2 is compared with the minimum impedance measurement for the initial stage 2, and, if this impedance measurement for the repeated stage 2 is greater than the minimum impedance measurement for the initial stage 2, then the seal is considered to be complete. A voltage level is then maintained and then the application is terminated.

If, however, the minimum impedance measurement of the repeated stage 2 is lower than the minimum impedance measurement of the initial stage 2, then the seal is not considered to be complete, and stage 3 is repeated.

Stages 2 and 3 are repeated until the minimum recorded impedance measurement of a repeated stage 2 is greater than the overall minimum recorded minimum impedance measurement of the previous stage 2s. In one example, the process may have a short off period between stage 3 and a repeating stage 2.

When the minimum recorded impedance measurement is greater than the overall minimum recorded minimum impedance measurement, the application of the radio frequency energy proceeds to stages 4 and 6, as shown in FIGS. 5 and 6.

During the application process, the system monitors for open circuit faults, using the impedance measurements. If the impedance measurements are above a predetermined threshold value for a predetermined time period, an open-circuit condition is detected. For example, if the impedance is consistently above 1500 R to 3000 R for periods of 200 ms to 500 ms, then an open circuit is detected.

Similarly, during the application process, the system monitors for short circuit faults, using current measurements. If the current flow is greater than a predetermined threshold value for a predetermined time period, then a short-circuit condition is detected. The current threshold value is set to be higher than the current supplied during normal operating times. For example, if the current is consistently above 4.5 A RMS, for periods of 400 ms, then a short circuit is detected. Upon detection of a short circuit, the radio frequency power is shut off In such a manner, an embodiment of the present invention is able to provide improved vessel sealing characteristics for a bipolar electrosurgical instrument.

The invention claimed is:

1. An electrosurgical system comprising:
a bipolar electrosurgical instrument comprising:
   a body;
   an elongate shaft (1) attached to the body and (2) having a distal end;
   first and second elongate jaw members at the distal end of the elongate shaft, the first elongate jaw member carrying a first electrode and the second elongate jaw member carrying a second electrode, the first and second elongate jaw members being movable relative to one another between an open position in which the first and second electrodes are spaced apart from one another, and a closed position in which the first electrode is adjacent the second electrode; and
   a power cable having (1) a pair of electrically conductive elements, (2) a first end for connection with a source of radio frequency electromagnetic energy, and (3) a second end for connection to the first and second electrodes; and
   a waveform generator which is the source of radio frequency electromagnetic energy and is connected with the power cable of the bipolar electrosurgical instrument, and comprising:
      a radio frequency signal generator configured to supply a radio frequency signal to the first and second electrodes via the power cable; and
      a controller configured to control operation of the radio frequency signal generator, in dependence upon a received control input,
   wherein the controller is configured, in a heating stage:
      to control the radio frequency signal generator to supply the radio frequency signal at a controlled voltage level to the first and second electrodes, the controlled voltage level starting at a starting voltage at a heating start time, and ending at a final voltage at a heating end time;
      to measure an impedance between the first and second electrodes during supply of the controlled voltage level and to record the impedance as a recorded impedance measurement;
      to detect a minimum measured impedance between the first and second electrodes during the heating stage, and to store the minimum measured impedance as a minimum recorded impedance measurement for the heating stage; and
      to determine the heating end time as a time when the recorded impedance measurement for the heating stage is greater than the minimum recorded impedance measurement by a threshold amount,
   wherein the controller is configured, in a sealing stage following the heating stage:
      to supply the radio frequency signal at a predetermined sealing voltage level to the first and second electrodes for a predetermined sealing time period having a sealing end time;
      to measure an impedance level between the first and second electrodes at the sealing end time;
      to compare the measured impedance with a predetermined reference impedance to produce a comparison signal; and
      to determine a next mode of operation for the radio frequency signal generator in dependence upon the comparison signal, and
   wherein the controller is configured, subsequent to the sealing stage:
      to repeat the heating and sealing stages when the minimum recorded impedance measurement for a repeated heating stage is lower than or equal to an overall minimum impedance measurement of a previous heating stage when there is only one previous heating stage or all previous heating stages when there are two or more previous heating stages, and
      to end the heating and sealing stages when the minimum recorded impedance measurement for the repeated heating stage is greater than the overall minimum impedance measurement of the previous heating stage or the all previous heating stages.

2. An electrosurgical system as claimed in claim 1, wherein the controller is configured, in an initialisation stage prior to the heating stage:
   to control the radio frequency signal generator to supply the radio frequency signal of a predetermined initial power level to the first and second electrodes for a predetermined initial time period having an end time;
   to measure a voltage level between the first and second electrodes at the end time; and
   to store the voltage level as a starting voltage for the heating stage.

3. An electrosurgical system as claimed in claim 1, wherein the controller is configured, in a completion stage subsequent to the ending of the heating and sealing stages:
   to control the radio frequency signal generator to apply the radio frequency signal at a predetermined completion voltage level, lower than the predetermined sealing voltage level, for a predetermined completion time period; and
   to end supply of the radio frequency signal.

4. An electrosurgical system as claimed in claim 1, wherein the controller is configured to measure electrical current supplied to the first and second electrodes to generate a measured current signal, and to detect a short circuit between the first and second electrodes if the measured current signal exceeds a first predetermined value for at least a predetermined time period.

5. An electrosurgical system as claimed in claim 1, wherein the threshold amount is an absolute value of impedance.

6. An electrosurgical system as claimed in claim 1, wherein the threshold amount is a relative value related to the minimum recorded impedance measurement.

7. A method of operating an electrosurgical system comprising a bipolar electrosurgical instrument comprising a body; an elongate shaft (1) attached to the body and (2) having a distal end; first and second elongate jaw members at the distal end of the elongate shaft, the first elongate jaw member carrying a first electrode and the second elongate jaw member carrying a second electrode, the first and second elongate jaw members being movable relative to one another between an open position in which the first and second electrodes are spaced apart from one another, and a closed position in which the first electrode is adjacent the second electrode; and a power cable having (1) a pair of electrically conductive elements, (2) a first end for connection with a source of radio frequency electromagnetic energy, and (3) a second end for connection to the first and second electrodes; and a waveform generator which is the source of radio frequency electromagnetic energy and is connected with the power cable of the bipolar electrosurgical instrument and comprising a radio frequency signal generator configured to supply a radio frequency signal to the first and second electrodes via the power cable; and a controller configured to control operation of the radio frequency signal generator, in dependence upon a received control input, wherein the method comprises:

a heating stage comprising:
controlling the radio frequency signal generator to supply the radio frequency signal at a controlled voltage level to the first and second electrodes, the controlled voltage level starting at a starting voltage at a heating start time, and ending at a final voltage at a heating end time;
measuring an impedance between the first and second electrodes during supply of the controlled voltage level and recording the impedance as a recorded impedance measurement;
detecting a minimum measured impedance between the first and second electrodes during the heating stage, and to store the minimum measured impedance as a minimum recorded impedance measurement for the heating stage; and
determining the heating end time as a time when the recorded impedance measurement for the heating stage is greater than the minimum recorded impedance measurement by a threshold amount, subsequent to the heating stage, a sealing stage comprising:
supplying the radio frequency signal at a predetermined sealing voltage level to the first and second electrodes for a predetermined sealing time period having a sealing end time;
measuring an impedance level between the first and second electrodes at the sealing end time;
comparing the impedance level with a predetermined reference impedance to produce a comparison signal; and determining a next mode of operation for the radio frequency generator in dependence upon the comparison signal; and subsequent to the sealing stage, repeating the heating and sealing stages when the minimum recorded impedance measurement for a repeated heating stage is lower than or equal to an overall minimum impedance measurement of a previous heating stage when there is only one previous heating stage or all previous heating stages when there are two or more previous heating stages, and ending the heating and sealing stages when the minimum recorded impedance measurement for the repeated heating stage is greater than the overall minimum impedance measurement of the previous heating stage or the all previous heating stages.

8. A method as claimed in claim 7, further comprising, in advance of the heating stage, an initialisation stage comprising:
supplying the radio frequency signal of a predetermined initial power level to the first and second electrodes for a predetermined initial time period having an initialisation end time;
measuring a voltage level between the first and second electrodes at the initialisation end time; and
storing the voltage level as a starting voltage for the heating stage.

9. A method as claimed in claim 7, further comprising, subsequent to the sealing stage, a completion stage comprising:
controlling the radio frequency signal generator to apply the radio frequency signal at a predetermined completion voltage level, lower than the predetermined sealing voltage level, for a predetermined completion time period; and
ending supply of the radio frequency signal.

10. A method as claimed in claim 7, further comprising measuring electrical current supplied to the first and second electrodes to generate a measured current signal and detecting a short circuit between the first and second electrodes if the measured current signal exceeds a first predetermined value for at least a predetermined time period.

11. A method as claimed in claim 7, wherein the threshold amount is an absolute value of impedance.

12. A method as claimed in claim 7, wherein the threshold value is a relative value related to the minimum recorded impedance measurement.

* * * * *